US010213194B2

(12) United States Patent
Kiturkes et al.

(10) Patent No.: US 10,213,194 B2
(45) Date of Patent: Feb. 26, 2019

(54) SURGICAL RETRACTION SYSTEMS INCLUDING STERNAL RETRACTORS AND HEMOSTATIC INSERTS

(71) Applicant: Ethicon, Inc., Somerville, NJ (US)

(72) Inventors: Alex W. Kiturkes, Mountain View, CA (US); James T. Spivey, Whitehouse Station, NJ (US)

(73) Assignee: Ethicon, Inc., Somerville, NJ (US)

( * ) Notice: Subject to any disclaimer, the term of this patent is extended or adjusted under 35 U.S.C. 154(b) by 303 days.

(21) Appl. No.: 15/277,736

(22) Filed: Sep. 27, 2016

(65) Prior Publication Data

US 2018/0085107 A1 Mar. 29, 2018

(51) Int. Cl.
*A61B 17/02* (2006.01)
*A61B 17/00* (2006.01)
*A61B 90/00* (2016.01)

(52) U.S. Cl.
CPC .......... *A61B 17/0293* (2013.01); *A61B 17/02* (2013.01); *A61B 17/0206* (2013.01); *A61B 2017/00473* (2013.01); *A61B 2017/00477* (2013.01); *A61B 2017/00862* (2013.01); *A61B 2017/00884* (2013.01); *A61B 2017/00893* (2013.01); *A61B 2017/0237* (2013.01); *A61B 2017/0287* (2013.01); *A61B 2090/08021* (2016.02)

(58) Field of Classification Search
CPC . A61B 17/02; A61B 17/0206; A61B 17/0293; A61B 2017/0212; A61B 2017/0237; A61B 2017/0243
See application file for complete search history.

(56) References Cited

U.S. PATENT DOCUMENTS 5,772,583 A 6/1998 Wright et al.
6,382,211 B1 5/2002 Crook
(Continued)

FOREIGN PATENT DOCUMENTS

CN 102333491 1/2012
EP 2572646 3/2013
(Continued)

OTHER PUBLICATIONS

International Search Report issued in corresponding PCT/US2017/051955, dated Nov. 2, 2017, 5 pages.

*Primary Examiner* — Eric S Gibson
(74) *Attorney, Agent, or Firm* — Doherty IP Law Group LLC

(57) ABSTRACT

A surgical retraction system includes a sternal retractor having a first retractor arm and a second retractor arm. An insert is coupled with the sternal retractor. The insert includes a first section having a first rigid backing, a second section having a second rigid backing that is spaced from the first rigid backing, and a connector section including resilient material interconnecting proximal ends of the first and second sections. The first section of the insert is coupled with the first retractor arm, the second section of the insert is coupled with the second retractor arm, and the connector section extends laterally between the proximal ends of the first and second sections. When the insert is bent, the resilient connector section normally urges the first and second sections of the insert away from one another for returning the insert to a flat configuration.

21 Claims, 12 Drawing Sheets

(56) References Cited

U.S. PATENT DOCUMENTS

| | | | |
|---|---|---|---|
| 6,390,976 B1* | 5/2002 | Spence | A61B 17/02 600/201 |
| 6,939,297 B2* | 9/2005 | Gannoe | A61B 17/02 600/232 |
| 7,238,154 B2 | 7/2007 | Ewers et al. | |
| 8,105,234 B2 | 1/2012 | Ewers et al. | |
| 8,118,738 B2* | 2/2012 | Larkin | A61B 1/303 600/222 |
| 8,262,568 B2 | 9/2012 | Albrecht et al. | |
| 8,357,086 B2 | 1/2013 | Kahle et al. | |
| 8,758,236 B2 | 6/2014 | Albrecht et al. | |
| 8,777,849 B2* | 7/2014 | Haig | A61B 17/0206 600/206 |
| 8,888,693 B2 | 11/2014 | Bonadio et al. | |
| 8,932,214 B2 | 1/2015 | Hart et al. | |
| 9,039,610 B2* | 5/2015 | Wilkins | A61B 17/0293 600/206 |
| 9,999,414 B2* | 6/2018 | Ruppert | A61B 17/0206 |
| 2002/0077532 A1* | 6/2002 | Gannoe | A61B 17/02 600/232 |
| 2004/0186354 A1* | 9/2004 | LiDonnici | A61B 1/32 600/210 |
| 2005/0155611 A1 | 7/2005 | Vaugh et al. | |
| 2005/0228447 A1 | 10/2005 | Rambo | |
| 2005/0241647 A1 | 11/2005 | Nguyen et al. | |
| 2007/0255219 A1 | 11/2007 | Vaugh et al. | |
| 2009/0069634 A1* | 3/2009 | Larkin | A61B 1/303 600/222 |
| 2012/0157786 A1 | 6/2012 | Pribanic | |
| 2012/0296170 A1* | 11/2012 | Wilkins | A61B 17/0293 600/206 |
| 2013/0012782 A1 | 1/2013 | Stearns et al. | |
| 2013/0060094 A1 | 3/2013 | Lee | |
| 2013/0237769 A1 | 9/2013 | Puskas | |
| 2014/0066953 A1* | 3/2014 | Keating | A61B 17/3423 606/130 |
| 2014/0303664 A1 | 10/2014 | Beck et al. | |
| 2015/0057504 A1* | 2/2015 | Vayser | A61B 90/35 600/249 |
| 2015/0148614 A1* | 5/2015 | Moshinsky | A61B 17/0218 600/210 |
| 2015/0209022 A1* | 7/2015 | Ruppert | A61B 17/0206 600/219 |
| 2018/0085107 A1* | 3/2018 | Kiturkes | A61B 17/0293 |
| 2018/0235592 A1* | 8/2018 | Kass | A61B 17/0206 |

FOREIGN PATENT DOCUMENTS

| | | |
|---|---|---|
| EP | 2547270 | 9/2015 |
| EP | 2152175 | 10/2015 |
| GB | 287529 | 12/1928 |

* cited by examiner

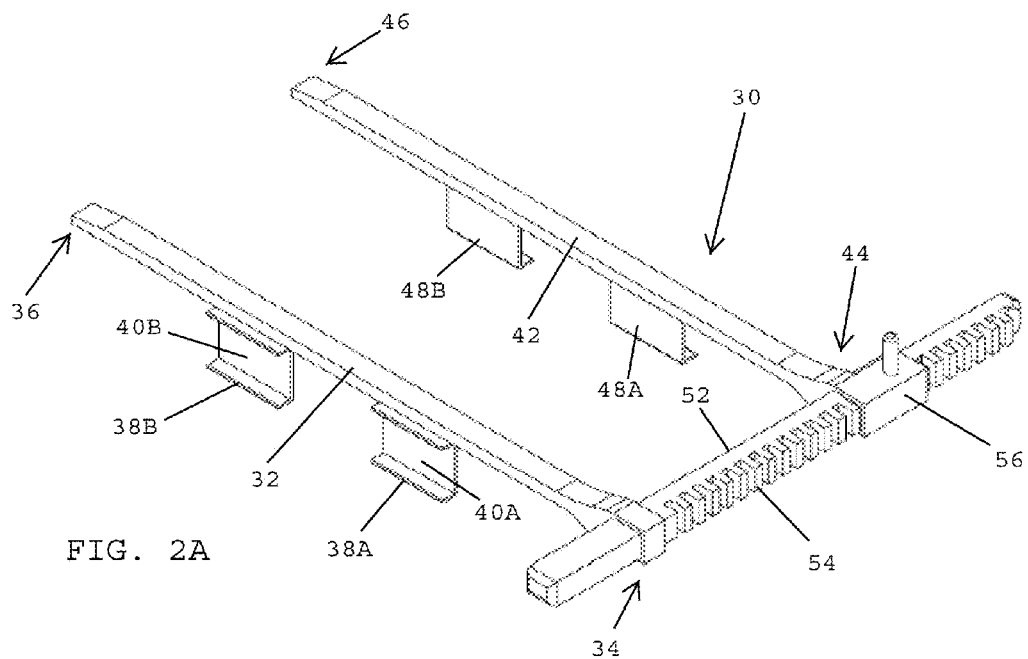
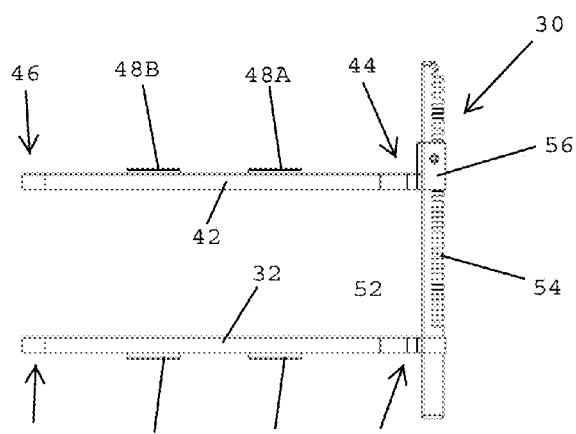
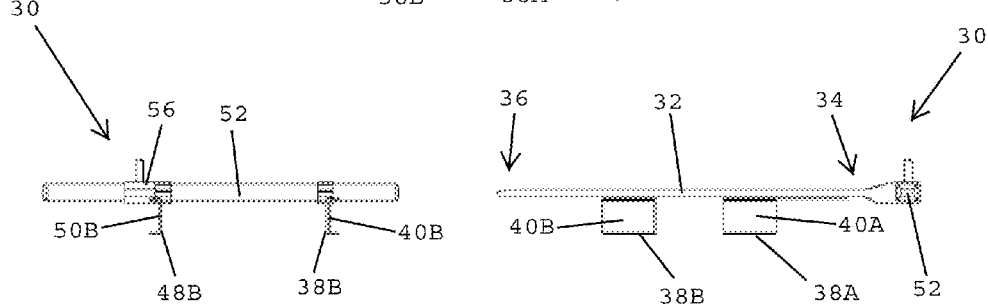

SURGICAL RETRACTION SYSTEMS INCLUDING STERNAL RETRACTORS AND HEMOSTATIC INSERTS

BACKGROUND OF THE INVENTION

Field of the Invention

The present patent application is generally related to surgical instruments and procedures, and is more specifically related to surgical retractors and medical devices used during open chest surgery.

Description of the Related Art

The sternum is a bone in the middle of the chest to which all of a patient's ribs are directly or indirectly attached. During open chest surgery (e.g., cardiac surgery), a chest saw or other cutting instrument is used to make a midline, longitudinal incision along the length of the patient's sternum to allow for lateral separation of the two opposing halves of the sternum. Typically, a sternal retractor is used to laterally separate the two opposing halves of the sternum.

Most sternal retractors have two arms that are attached to a rack and pinion mechanism. One of the arms is fixed and the other arm is movable via the rack and pinion mechanism. Each arm carries a blade or flange having a sternal engaging surface. After the sternum is cut, the blades are inserted into the cut opening so that the sternal engaging surfaces on the blades rest against the opposing cut edges of the sternum. The rack and pinion mechanism is operated to move the blades away from each other, which, in turn, causes the cut sternal edges to move away from each other. The blade movement continues until the sternal opening is sufficiently large to provide a surgeon with access to a surgical site within the chest cavity.

The ribs attached to the top of the sternum are generally shorter than the ribs attached to the bottom of the sternum. As a result, when the chest is opened using a sternal retractor, more stress may be placed on the shorter, upper ribs than the longer, lower ribs, which can cause various problems including fractures, broken ribs, bleeding, infection, and improper or slow healing.

In many instances, the loss of blood from the cut edges of the sternum may obstruct and/or obliterate the view of the surgical team when performing a surgical procedure. In response, wax and gel substances have been developed that are applied to the bleeding surfaces of the cut sternum. These wax and gel substances generally inhibit and/or otherwise reduce bleeding, however, after the surgery is complete, the wax and gel substances are left in the sternum (i.e., between the cut halves of the sternum), which may result in contamination of blood cells, infection, and improper or slow healing.

There have been numerous efforts directed to providing retractor systems that minimize bleeding of the opposing cut edges of a sternum, reduce fractures or broken bones at the cut edges of a sternum, minimize the likelihood of infection, and promote rapid and proper healing of the rejoined sternal edges.

For example, US 2013/0237769 to Puskas discloses devices and methods for sternal retraction that reduce bleeding from the cut edges of a sternum and reduce fracturing of the sternum during retraction. The Puskas device uses sternal retractor blades having a certain geometry and inserts that are placed inside the sternal retractor blades to tamponade blood flow from the cut sternal edges, which also reduces fracturing of the sternum during retraction.

US 2014/0303664 to Beck et al. discloses an atraumatic sternal plate for a sternal retractor with a pressure plate and a retaining device attached to the pressure plate. The pressure plate can be attached, by means of the retaining device, to either the blades of a retractor or to a sternal half of the patient, so that the pressure plate abuts the sagittal incision surface of a sternal half when spreading the sternum of a patient using a retractor.

US 2004/0186354 to LiDonnici discloses methods and devices for minimizing bleeding from the exposed ends of cut sternal halves during cardiac and/or thoracic surgical procedures. The device includes an end wall having a size and a dimension to at least partially cover the exposed end of a sternal half. The device has an upper wall, a lower wall spaced from the upper wall, and an end wall interconnecting the upper and lower walls. The upper wall, the lower wall, and the end wall define a space into which an exposed end of a sternal half is received.

In spite of the above advances, there remains a need for improved inserts for use with surgical retractors, improves sternal retractor systems, and enhanced surgical procedures that minimize bleeding, infection, complications, and the likelihood of fractures, that reduce patient discomfort, and that promote rapid healing following open chest surgery.

SUMMARY OF THE INVENTION

In one embodiment, a surgical retraction system includes a sternal retractor having a first retractor arm and a second retractor arm. In one embodiment, the system includes an insert with a first section having a first rigid backing, a second section having a second rigid backing that is spaced from the first rigid backing, and a connector section made of resilient material interconnecting proximal ends of the first and second sections. In one embodiment, the first section of the insert is coupled with the first retractor arm, the second section of the insert is coupled with the second retractor arm, and the connector section of the insert extends laterally between the proximal ends of the first and second sections of the insert.

In one embodiment, the connector section of the insert is flexible for enabling the insert to flex between a flat configuration and a bent configuration. In one embodiment, the resilient connector section normally urges the insert into the flat configuration when the first and second sections of the insert are unconstrained.

In one embodiment, the first retractor arm has at least one first arm flange and the first section of the insert is connected with the at least one first arm flange. In one embodiment, the second retractor arm has at least one second arm flange and the second section of the insert is connected with the at least one second arm flange.

In one embodiment, the first rigid backing includes a plurality of first malleable tabs, and the second rigid backing includes a plurality of second malleable tabs. In one embodiment, a first metal sleeve is connected with the first rigid backing, and the first metal sleeve includes the first malleable tabs. In one embodiment, a second metal sleeve is connected with the second rigid backing, and the second metal sleeve includes the second malleable tabs.

In one embodiment, one or more of the first malleable tabs are in contact with (e.g., bent over) the at least one first arm flange for securing the first section of the insert to the first retractor arm. In one embodiment, one or more of the second malleable tabs are in contact with (e.g., bent over) the at least one second arm flange for securing the second section of the insert to the second retractor arm.

In one embodiment, the insert, when in the bent configuration, has a U-shape with the first section of the insert forming a first vertical leg of the U-shape, the second section of the insert forming a second vertical leg of the U-shape, and the connector section forming a curved base of the U-shape that extends laterally between the proximal ends of the first and second sections.

In one embodiment, when the insert is in a flat configuration, the first section of the insert, the second section of the insert, and the connector section of the insert lie in a common plane.

In one embodiment, the insert includes a flexible backing having a first major surface, a second major surface, a first end defining the first section of the insert, a second end defining the second section of the insert, and the connector section interconnecting the first and second ends of the flexible backing.

In one embodiment, a first rigid member is aligned with the first end of the flexible backing and attached to the second major surface of the flexible backing to form the first rigid backing of the first section of the insert, and a second rigid member is aligned with the second end of the flexible backing and attached to the second major surface of the flexible backing to form the second rigid backing of the second section.

In one embodiment, a first layer of material containing the hemostatic agent covers the first major surface of the flexible backing at the first end of the flexible backing, and a second layer of material containing the hemostatic agent covers the first major surface of the flexible backing at the second end of the flexible backing.

In one embodiment, an insert includes a second connector section interconnecting distal ends of the first and second sections of the insert. In one embodiment, the second connector section includes resilient material. In one embodiment, the insert has an oval shape and the first and second connector sections are flexible for allowing the first and second sections of the insert to be compressed toward one another for collapsing the oval for placement between the opposing edges of cut bone. When the compression force is released, the first and second connector sections are resilient for returning the insert to the oval shape.

In one embodiment, a surgical retraction system includes a sternal retractor having a first retractor arm and a second retractor arm and an insert adapted to be coupled with the sterna retractor. In one embodiment, the insert includes a flexible backing having a front surface, a back surface, a first end, a second end, and a connector section interconnecting the first and second ends of the flexible backing. In one embodiment, a first rigid member is aligned with the first end of the flexible backing and attached to the back surface of the flexible backing to form a first rigid section of the insert, and a second rigid member is aligned with the second end of the flexible backing and attached to the back surface of the flexible backing to form a second rigid section of the insert. In one embodiment, the first rigid section of the insert is coupled with the first retractor arm, the second rigid section of the insert is coupled with the second retractor arm, and the connector section extends laterally between proximal ends of the first and second rigid sections.

In one embodiment, the connector section includes a resilient material that normally urges the first and second rigid sections of the insert away from one another.

In one embodiment, the insert is bendable from a flat configuration to a bent configuration. In one embodiment, the resilient connector section normally returns the insert back to the flat configuration when the first and second rigid sections of the insert are unconstrained. Thus, the resilient connector section of the insert can be bent or folded for placement between the opposing cut edges of bone (e.g., a cut sternum) and the resilient connector section will hold the insert in place as it urges the insert to return to the flat configuration.

In one embodiment, when the insert is in the bent configuration, the insert has a U-shape with the first rigid section of the insert forming a first vertical leg of the U-shape, the second rigid section of the insert forming a second vertical leg of the U-shape, and the resilient connector section forming a curved base of the U-shape that extends laterally between the proximal ends of the first and second rigid sections.

In one embodiment, the insert has a first layer of material including a hemostatic agent covering the first rigid section of the insert, and a second layer of material including a hemostatic agent covering the second rigid section of the insert.

In one embodiment, the first rigid member has a plurality of first malleable tabs, and the second rigid member has a plurality of second malleable tabs. In one embodiment, one or more of the first malleable tabs are in contact with (e.g., bent over, folded over, wrapped around) the first retractor arm or at least one of the first arm flanges for securing the first rigid member to the first retractor arm, and one or more of the second malleable tabs are in contact with (e.g., bent over, folded over, wrapped around) the second retractor arm or at least one of the second arm flanges for securing the second rigid member to the second retractor arm.

In one embodiment, a surgical retraction system includes a sternal retractor having a first retractor arm with at least one first arm flange and a second retractor arm having at least one second arm flange, and an insert assembled with the sternal retractor. In one embodiment, the insert includes a first section having a first rigid backing, the first rigid backing having one or more first malleable tabs in contact with the at least one first arm flange for securing the first section of the insert to the first retractor arm, and a second section having a second rigid backing that is spaced from the first rigid backing, the second rigid backing having one or more second malleable tabs in contact with the at least one second arm flange for securing the second section of the insert to the second retractor arm. In one embodiment, the insert has a flexible connector section interconnecting proximal ends of the first and second sections of the insert. In one embodiment, the connector section includes a resilient material.

In one embodiment, a second flexible connector section interconnects distal ends of the first and second sections of the insert. The second connector section includes a resilient material. In one embodiment the insert has an oval shape, and the first and second connector sections are flexible for allowing the first and second sections of the insert to be compressed toward one another for being inserted between the opposing edges of cut bone, such as the opposing edges of a split sternum.

In one embodiment, an insert for a sternal retractor includes a first section having a first rigid backing, a second section having a second rigid backing that is spaced from the first rigid backing, and a connector section including resilient material interconnecting proximal ends of the first and second sections. In one embodiment, the connector section of the insert is flexible for bending the insert from a flat configuration to a bent configuration. In one embodiment, the connector section includes resilient material that normally returns the insert back to the flat configuration when the first and second sections of the insert are unconstrained. In one embodiment, the first and second sections of the insert include a hemostatic agent (e.g., Surgical®).

In one embodiment, the first rigid backing includes a plurality of first malleable tabs that are bendable, and the second rigid backing includes a plurality of second malleable tabs that are bendable. In one embodiment, the insert includes a first metal sleeve connected with the first rigid backing, the first metal sleeve having the first malleable tabs. In one embodiment, the insert includes a second metal sleeve connected with the second rigid backing, the second metal sleeve having the second malleable tabs.

In one embodiment, when the insert is in the bent configuration, the insert has a U-shape with the first section of the insert forming a first vertical leg of the U-shape, the second section of the insert forming a second vertical leg of the U-shape, and the connector section forming a curved base of the U-shape that extends laterally between the proximal ends of the first and second sections.

In one embodiment, when the insert is in the flat configuration, the first section, the second section, and the connector section of the insert lie in a common plane.

In one embodiment, the insert includes a flexible backing that forms a core of the insert. In one embodiment, the flexible backing has a first major surface, a second major surface, a first end defining the first section of the insert, a second end defining the second section of the insert, and the connector section interconnecting the first and second ends of the flexible backing.

In one embodiment, the insert includes a first rigid member aligned with the first end of the flexible backing and attached to the second major surface of the flexible backing to form the first rigid backing of the first section of the insert, and the insert includes a second rigid member aligned with the second end of the flexible backing and attached to the second major surface of the flexible backing to form the second rigid backing of the second section.

In one embodiment, the insert has a first layer of material containing a hemostatic agent covering the first major surface of the flexible backing at the first end of the flexible backing, and a second layer of material containing the hemostatic agent covering the first major surface of the flexible backing at the second end of the flexible backing.

In one embodiment, an insert for a sternal retractor includes a second connector section including resilient material interconnecting distal ends of the first and second sections. In one embodiment, the first and second connector sections form an insert having an oval shape, whereby the first and second connector sections are flexible for allowing the first and second sections of the insert to be compressed toward one another.

In one embodiment, the insert is used as part of a system that includes a sternal retractor. In one embodiment, the system includes a sternal retractor having a first retractor arm and a second retractor arm, whereby the insert is in a bent configuration with the first section of the insert coupled with the first retractor arm, the second section of the insert coupled with the second retractor arm, and the connector section extending laterally between the proximal ends of the first and second sections.

In one embodiment, the first retractor arm has at least one first arm flange, whereby the first section of the insert is connected with the at least one first arm flange, and the second retractor arm has at least one second arm flange, whereby the second section of the insert is connected with the at least one second arm flange.

In one embodiment, one or more of the first malleable tabs are bent over the at least one first arm flange for connecting the first section of the insert with the first retractor arm, and one or more of the second malleable tabs are bent over the at least one second arm flange for connecting the second section of the insert with the second retractor arm.

In one embodiment, an insert for a sternal retractor includes a flexible backing having a front surface, a back surface, a first end, a second end, and a connector section interconnecting the first and second ends of the flexible backing. In one embodiment, a first rigid member is aligned with the first end of the flexible backing and is attached to the back surface of the flexible backing to form a first rigid section of the insert. In one embodiment, a second rigid member is aligned with the second end of the flexible backing and is attached to the back surface of the flexible backing to form a second rigid section of the insert. In one embodiment, the insert is bendable from a flat configuration to a bent configuration, whereby the connector section includes a resilient material that normally returns the insert back to the flat configuration when the first and second rigid sections of the insert are unconstrained or released.

In one embodiment, the insert has a first layer of material containing a hemostatic agent that covers the first rigid section of the insert, and a second layer of material containing a hemostatic agent that covers the second rigid section of the insert. In one embodiment, the first rigid member includes a plurality of first malleable tabs, and the second rigid member includes a plurality of second malleable tabs.

In one embodiment, when the insert is in the bent configuration, the insert has a U-shape with the first rigid section of the insert forming a first vertical leg of the U-shape, the second rigid section of the insert forming a second vertical leg of the U-shape, and the flexible section forming a curved base of the U-shape that extends laterally between the proximal ends of the first and second rigid sections. In one embodiment, the first rigid section, the second rigid section, and the connector section of the insert lie in a common plane when the insert is in the flat configuration.

In one embodiment, a system used during open chest surgery includes a sternal retractor having a first retractor arm and a second retractor arm. In one embodiment, the insert is compressed into the bent configuration with the first rigid section of the insert being coupled with the first retractor arm, the second rigid section of the insert being coupled with the second retractor arm, and the connector section extending laterally between the proximal ends of the first and second rigid sections.

In one embodiment, an insert for a sternal retractor includes a first section having a first rigid backing, the first rigid backing including a plurality of first malleable tabs, and a second section having a second rigid backing that is spaced from the first rigid backing, the second rigid backing including a plurality of second malleable tabs. In one embodiment, a flexible connector section interconnects proximal ends of the first and second sections of the insert. In one embodiment the connector section includes a resilient material that returns the insert to a flat configuration when the first and second sections of the insert are released and/or unconstrained.

In one embodiment, an insert includes a second flexible connector section interconnecting distal ends of the first and second sections of the insert. In one embodiment, the second connector section includes a resilient material. In one embodiment, the insert has an oval shape. In one embodiment, the first and second connector sections are flexible for allowing the first and second sections of the insert to be compressed toward one another for placement between the opposing cut edges of a split sternum.

In one embodiment, when a hemostatic insert is used in conjunction with a sternal retractor having arms that move away from one another, the rigid members of the insert transfer spreading force from the arms of the sternal retractor to the split sternum to apply more even pressure on the opposing cut edges of the split sternum.

In one embodiment, the flexible backing material conforms to fit a variety of sternal retractors while also conforming to variable sternal surface geometry. The flexible backing material may be flexible, compliant and/or resilient.

In one embodiment, an insert includes a flexible backing having a first rigid section and a second rigid section with a flexible section positioned between and connected to the first and second rigid sections to allow for bending and/or folding of the insert into a U-shaped form. In one embodiment, the first rigid section is adapted to abut against a first arm of a retractor and the second rigid section is adapted to abut against a second arm of a retractor. The first and second sections may be covered with hemostatic or absorbent material.

In one embodiment, an insert for a sternal retractor has an oval or racetrack shape rather than a U-shape. In this embodiment, the first and second rigid sections are connected at proximal ends by a first flexible section and at distal ends by a second flexible section. The flexible sections have resiliency or spring-like characteristics that normally urge the first and second rigid sections away from one another. If the first and second rigid sections are collapsed toward one another (e.g., for insertion between the opposing cut edges of a sternum), the resiliency of the first and second flexible sections returns the insert back to its normal configuration after the collapsing force is released.

In one embodiment, an insert includes malleable metal tabs for attaching the insert to the arms of a surgical retractor. In one embodiment, the malleable metal tabs may be created using stamped out pieces that create the tabs. In operation, surgical personnel may place the malleable metal tabs against the arms of a retractor or attachment flanges extending from the arms of a retractor and wrap/fold the malleable tabs around the arms/flanges to further secure the insert in place on the arms of the retractor. The tabs provide enhanced attachment that prevents the insert from shifting relative to the arms of the retractor.

In one embodiment, the insert is connected with the arms of a surgical retractor via the blades or flanges on the retractor arms and the malleable tabs provide enhanced attachment of the insert to the blades of flanges of the retractor arms so that the insert does not move or shift relative to the attachment arms.

These and other preferred embodiments of inserts for sternal retractors will be described in more detail herein.

BRIEF DESCRIPTION OF THE DRAWING

FIGS. 2A-2D show a surgical retractor for use during open chest surgery.

DETAILED DESCRIPTION OF PREFERRED EMBODIMENTS

Figure 1A:
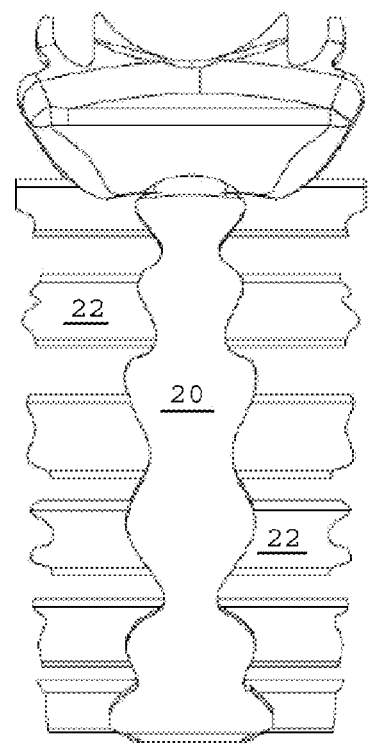
FIGS. 1A and 1B show a method of splitting a sternum for gaining access to a surgical site.

Referring to FIG. 1A, the sternum 20 is a bone in the middle of the chest that is attached either directly or indirectly to a patient's ribs 22. During open chest surgery, in order to gain access to a surgical site inside the chest cavity, the sternum 20 may be split using a cutting instrument such as a chest saw.

Figure 1B:
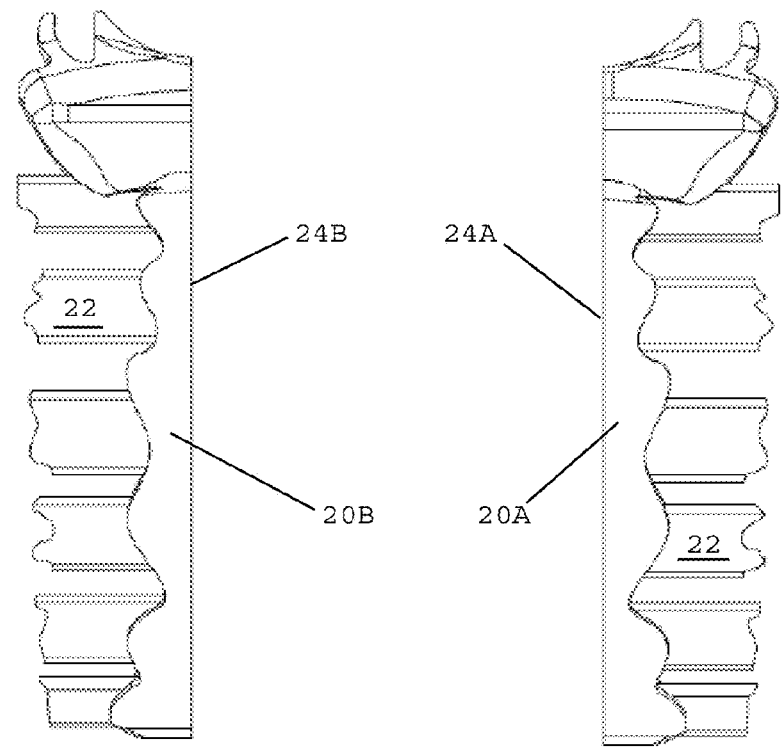

FIG. 1B shows the sternum 20 after it has been split into a first half 20A and a second half 20B. As will be described in more detail herein, a sternal retractor having first and second arms may be used to engage the opposing cut edges 24A, 24B of the sternum 20 for moving the first and second halves 20A, 20B of the sternum away from one another to increase the size of the surgical opening.

Referring to FIGS. 2A-2D, in one embodiment, a sternal retractor 30 includes a first arm 32 having a proximal end 34 and a distal end 36. The first arm 32 includes C-shaped flanges 38A, 38B having sternum contacting surfaces 40A, 40B that are adapted to engage the first cut edge 24A of the split sternum 20 (FIGS. 1A and 1B).

The retractor 30 includes a second arm 42 having a proximal end 44 and a distal end 46 remote therefrom. The second arm 42 includes a pair of C-shaped flanges 48A, 48B having sternum contacting surfaces 50A, 50B that are adapted to engage the second cut edge 24B of the split sternum 20 (FIGS. 1A and 1B). In one embodiment, the first arm 32 of the retractor 30 is stationary and the second arm 42 of the retractor is moveable toward and away from the first arm.

In one embodiment, the retractor includes a rack 52 having spaced teeth 54 and a pinion 56 coupled with the proximal end 44 of the second moveable arm 42. The retractor 30 desirably has an actuator (not shown) coupled with the pinion 56. In one embodiment, the proximal end 34 of the first arm 32 is secured to the rack 52 so that it is stationary relative to the rack 52. The actuator may be engaged for moving the second arm 42 away from the first arm 32 for increasing the distance between the first and second arms 32, 42, which, in turn, increase the space between the opposing cut edges 24A, 24B of the sternum 20 (FIGS. 1A and 1B).

Referring to FIGS. 1A-1B and 2A-2D, during an open chest surgical procedure, the sternum bone 20 is split and the C-shaped flanges 38A, 38B and 48A, 48B of the respective first and second arms 32, 42 of the retractor 30 are positioned between the opposing cut edges 24A, 24B of the sternum 20.

The sternum contacting surfaces 40A, 40B of the C-shaped flanges 38A, 38B on the first arm 32 engage the first half 20A of the split sternum 20 and the sternum contacting surfaces 50A, 50B of the C-shaped flanges 48A, 48B on the second arm 42 engage the opposite, second half 20B of the split sternum 20.

Figure 3A:
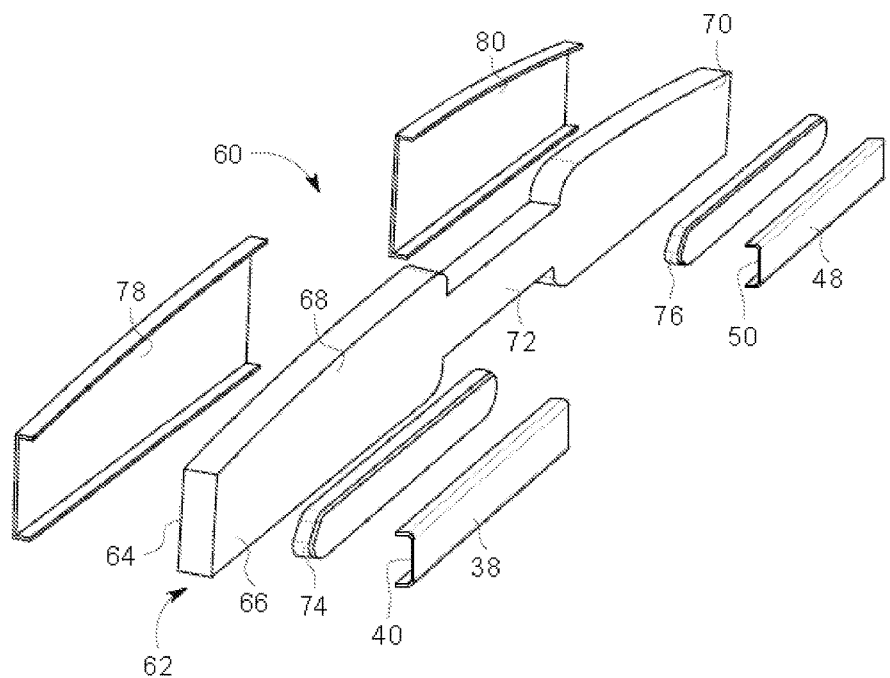
FIGS. 3A-3B show an exploded view of an insert for a sternal retractor, in accordance with one embodiment of the present invention.
Figure 3B:
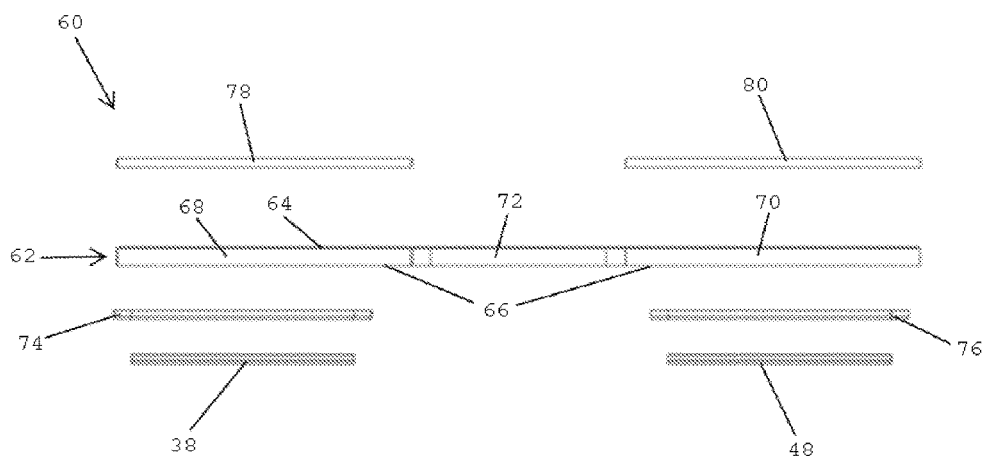

Referring to FIGS. 3A and 3B, in one embodiment, a hemostatic insert 60 is used with the sternal retractor disclosed herein. In one embodiment, the hemostatic insert 60 desirably includes a flexible backing 62, such as a foam layer, having a first major surface 64 (aka front surface) and a second major surface 66 (aka back surface). The flexible backing 62 desirably includes a first section 68 at a first end, a second section 70 at an opposite, second end, and a flexible, resilient connector section 72 that extends between and interconnects the first and second sections 68, 70.

In one embodiment, the flexible backing 62 has an overall length of about 12-18 inches, with the first section 68 having a length of about 4-8 inches, the second section 70 having a length of about 4-8 inches, and the connector section 72 having a length of about 2-4 inches. In one embodiment, the flexible backing 62 may be made of foam, rubber, silicone, elastomeric materials, and any combination thereof.

In one embodiment, the hemostatic insert 60 includes a first rigid member 74 that is secured to the second major surface 66 of the first section 68 of the flexible backing 62, and a second rigid member 76 that is secured to the second major surface 66 of the second section 70 of the flexible backing 62. The rigid members 74, 76 may be made of durable, biocompatible material such as stainless steel, aluminum, and/or plastic. In one embodiment, the rigid members 74, 76 may be made of any combination of stainless steel, aluminum, and plastic.

In one embodiment, the hemostatic insert 60 desirably includes a first hemostatic layer 78, such as Surgicel® or a similar material, that overlies the first major surface 64 of the first section 68 of the flexible backing 62, and a second hemostatic later 80, such as Surgicel® or a similar material, that overlies the first major surface 64 of the second section 70 of the flexible backing 62.

In one embodiment, the rigid members 74, 76 have lengths of about 4-6 inches and the first and second hemostatic layers 78, 80 have lengths of about 4-8 inches. The above dimensions are merely exemplary and other hemostatic inserts may have different lengths and/or dimensions.

FIGS. 3A and 3B show the C-shaped flanges 38, 40 of the retractor 30 (FIGS. 2A-2D), which are connected with the respective first and second arms 32, 42 of the sternal retractor 30. The C-shaped flanges do not form part of the insert, but are shown in FIGS. 3A and 3B to show the orientation of the insert relative to the arms of the retractor. As will be described in more detail herein, the sternum contacting surfaces 40A, 40B on the C-shaped flanges 38A, 38B engage the first rigid member 74 of the insert 60, and the sternum contacting surfaces 50A, 50B on the C-shaped flanges 48A, 48B engage the second rigid member 76 of the insert 60 to transmit a sternum separating force from the retractor arms to the hemostatic insert 60.

In one embodiment, the hemostatic layers 78, 80 may be made of biodegradable materials that are designed to stop bleeding, prevent infection, and promote healing. In one embodiment, the hemostatic layers 78, 80 comprise Surgicel® or similar materials that are treated with one or more solutions to prevent bleeding, prevent infection, and promote healing. Surgicel®, manufactured and sold by Ethicon, Inc., is made of an oxidized cellulose polymer and contains a hemostatic agent (i.e., a blood-clot-inducing material).

In one embodiment, the flexible backing 62 is normally flat as shown in FIGS. 3A and 3B. The flexible backing 62 desirably has resiliency or spring-like qualities so that if the connector section 72 is bent for bringing the first and second sections 68, 70 of the flexible backing 62 toward one another, the connector section 72 will normally return the flexible backing to flat configuration when the first and second sections 68, 70 of the flexible backing 62 are released. Although the present invention is not limited by any particular theory of operation, it is believed that providing a connector section 72 having resiliency or spring-like qualities, and which interconnects the first and second sections 68, 70 of a flexible backing 62, will assist surgical personnel in positioning and holding the hemostatic insert 60 between the opposing cut edges of a sternum. In the prior art, there is no interconnection or connector section between a first insert that engages a first side of a split sternum and a second insert that engages a second side of a split sternum. In the prior art, the separation of the first and second inserts into two separate and distinct parts makes it extremely difficult for surgical personnel to maintain the two separate insert parts in place and against the opposing cut edges of the sternum before the arms of a surgical retractor may be moved into position for engaging the two distinct insert parts. The resiliency or spring-like feature provided by the connector section provides the hemostatic insert disclosed herein with a self-seating capability, and the ability of the insert to hold its position between the two halves of the split sternum.

Figure 4:
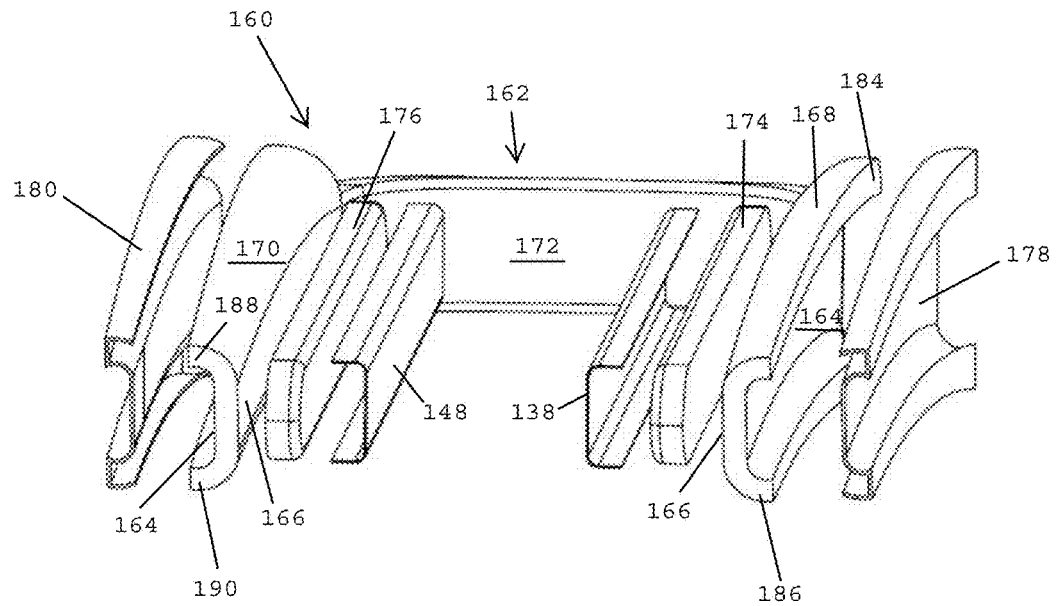
FIG. 4 shows an exploded view of an insert for a sternal retractor, in accordance with another embodiment of the present invention.

Referring to FIG. 4, in one embodiment, a hemostatic insert 160 for a sternal retractor desirably includes a flexible backing 162 having a first section 168 and a second section 170 that are interconnected by a connector section 172 having resiliency. The outer surface 164 (aka front surface) of the first section 168 that engages an edge of a split sternum is molded or formed to define a cross-section having a C-shape or trough-shape with an upper flange 184 and a lower flange 186. The hemostatic layer 178 overlying the first major surface 164 has a similar C-shape or trough shaped configuration. The outer surface 164 (aka front face) of the second section 170 that engages a split sternum is also molded or formed to provide a C-shape or trough-shaped surface with an upper flange 188 and a lower flange 190. A second hemostatic layer 180 overlies the outer surface 164 of the second section 170 and conforms to the trough or C-shaped configuration of the outer surface 164. In one embodiment, the cut edges of the split sternum are disposed within the C-shaped or trough-shaped surfaces and the flanges bound the cut halves both above and below for controlling bleeding and minimizing damage to the cuts halves.

In one embodiment, a first rigid member 174 is secured to the second major face 166 (i.e., back surface) of the first section 168 and a second rigid member 176 is secured to the second major face 166 (i.e., back surface) of the second section 170. In one embodiment, a C-shaped flange 138 of a first arm of a retractor is adapted to engage the first rigid member 174 and a C-shaped flange 148 of a second moveable arm of a retractor is adapted to engage the second rigid member 176. The rigid members 138, 148 transmit separating force from the arms of a surgical retractor and the respective first and second sections of the flexible backing 162. The rigid members also preferably spread out the force of the retractor arms so that it is not localized at any particular section of the opposing cut edges so as to minimize damage to the tissue and bone at the opposing cut edges.

Figure 5A:
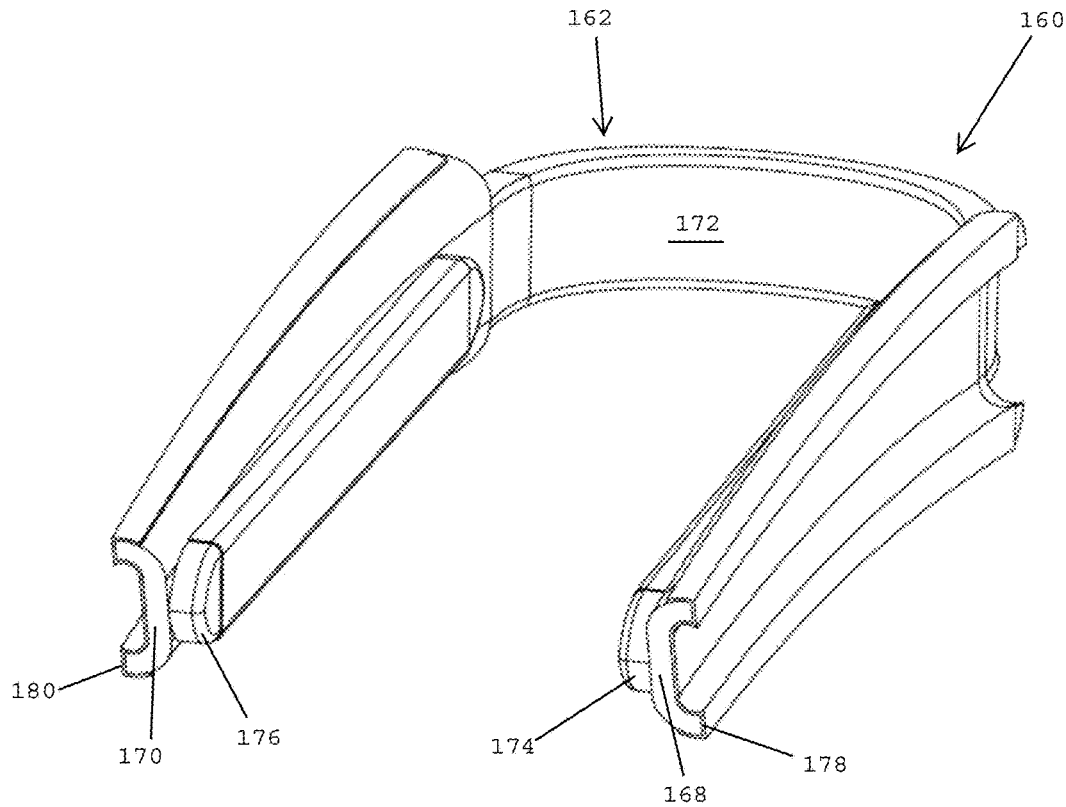
FIGS. 5A-5C show the insert of FIG. 4 after assembly.
Figure 5B:
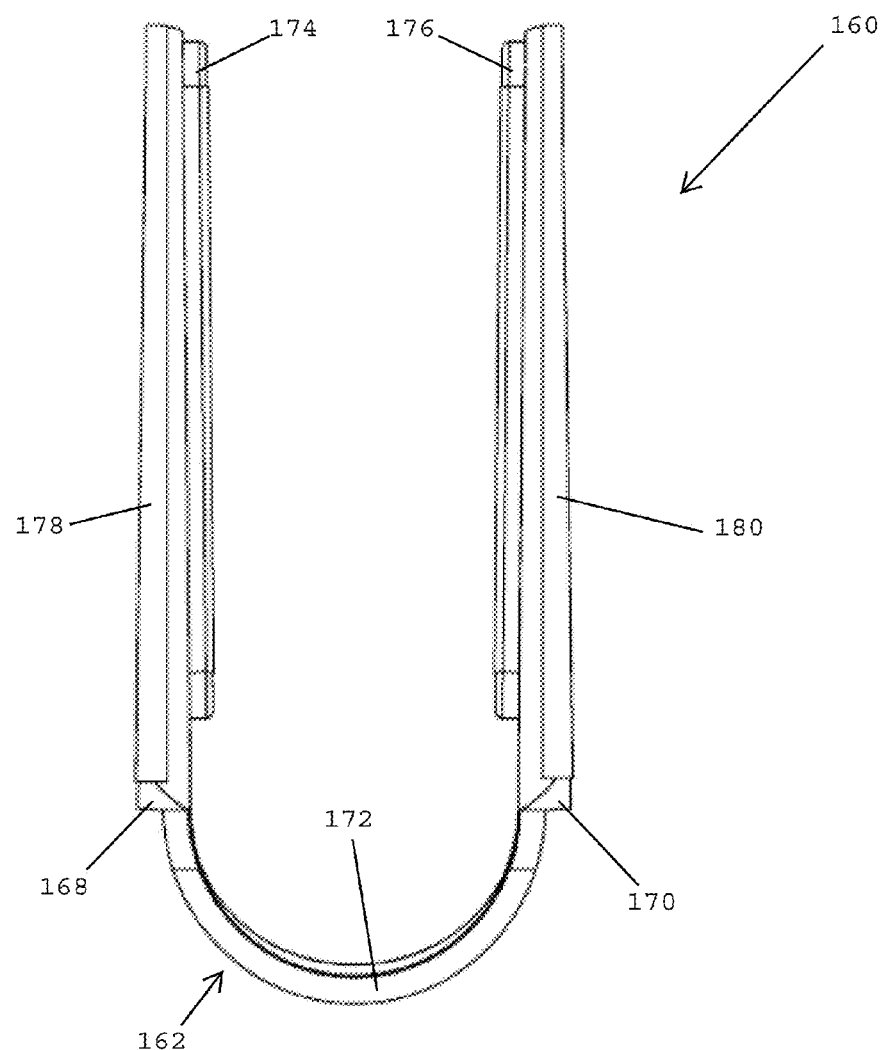
Figure 5C:
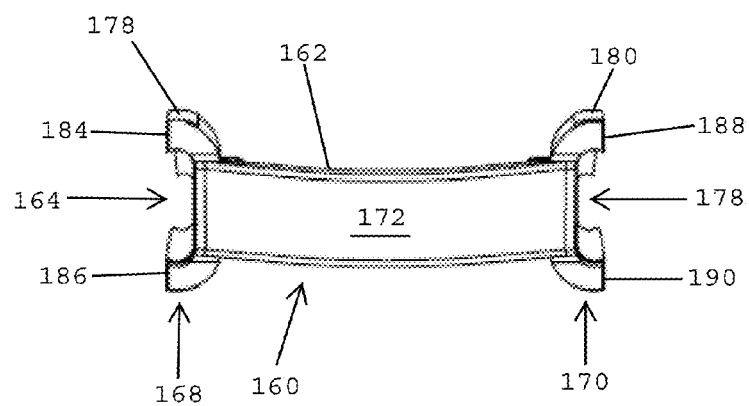

FIGS. 5B-5C show the hemostatic insert of FIG. 4 after it has been assembled. In one embodiment, the hemostatic insert 160 includes the flexible backing 162 having the first section 168 and the second section 170 interconnected by the connector section 172. In one embodiment, the split sternum engaging surfaces of the first and second sections (i.e., front surfaces) are molded or formed to have a C-shaped or trough-shaped configuration for cradling the cut edges of the sternum. In one embodiment, both split sternum engaging surfaces are covered with hemostatic layers 178, 180 (e.g., Surgical®), respectively, for controlling and/or minimizing bleeding. A first rigid member 174 is connected with the inner surface (i.e., back surface) of the first section 168 of the flexible backing 162 and a second rigid member 176 is connected with the inner surface (i.e., back surface) of the second section 170 of the flexible backing.

As noted above, the connector section 172 of the flexible backing 162 has resiliency and/or spring-like characteristics that enable the first and second sections 168, 170 to be collapsed and/or pressed inwardly toward one another, but that normally urge the first and second sections to move away from one another (when the collapsing force is removed) so that the flexible backing 162 returns to the flat configuration shown in FIGS. 3A and 3B. This resiliency and/or spring-like feature enables the insert to hold itself in place between the opposing cut edges of a sternum prior to the retractor arms being connected to the first and second sections 168, 170 of the insert.

Referring to FIG. 5C, in one embodiment, the first section 168 of the insert has the C-shaped or trough-shaped outer surface 164 that defines a trough located between an upper flange 184 and a lower flange 186. The second section 170 of the insert 160 has a similar molded outer surface that defines a trough 178 that extends between an upper flange 188 and a lower flange 190. In one embodiment, the opposing edges of the split sternum are disposed and/or cradled within the troughs 164, 178 of the first and second sections 168, 170 of the flexible backing 162 for controlling bleeding and minimizing damage to the cut edges.

Figure 6A:
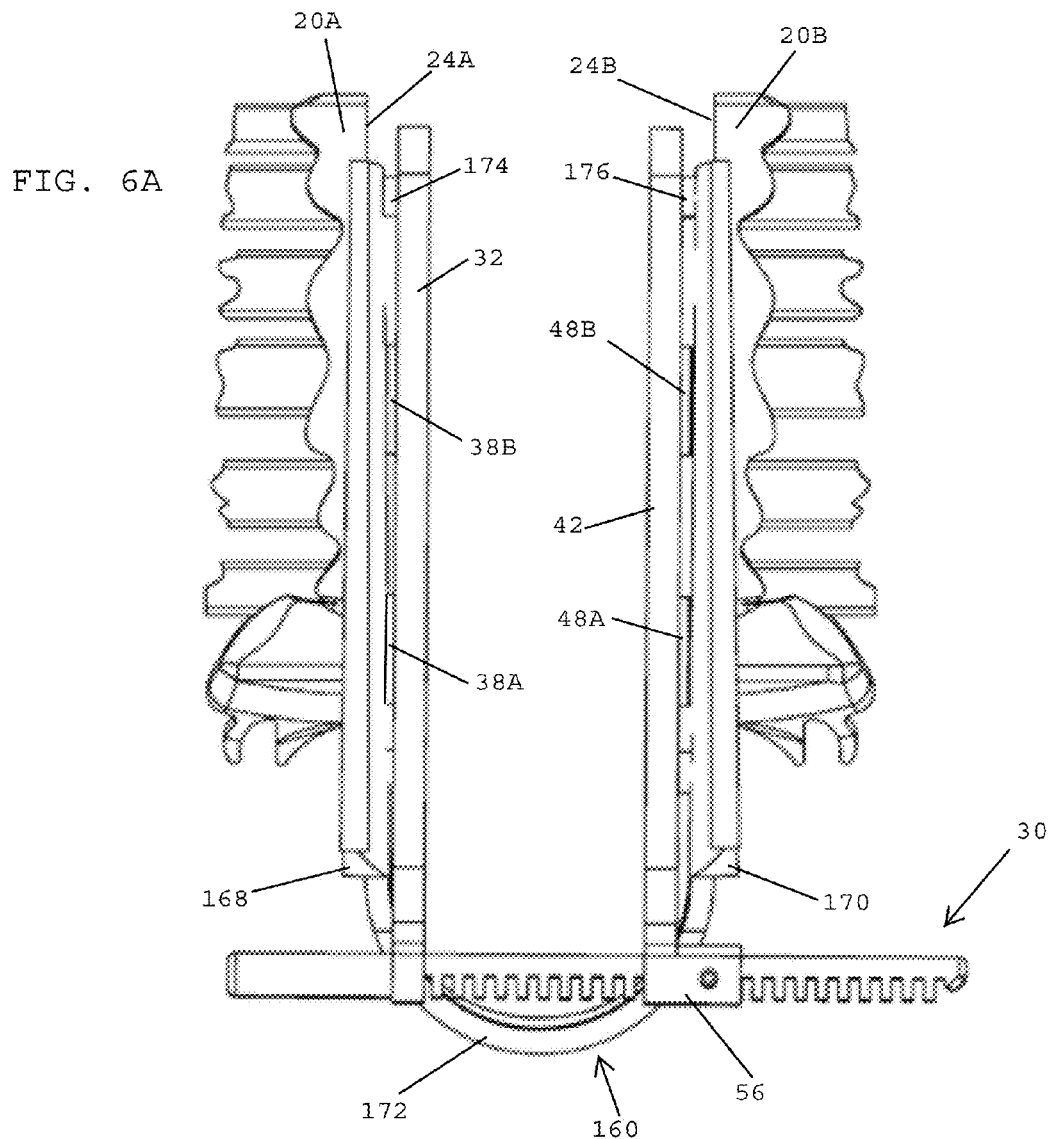
FIGS. 6A-6C show the insert of FIGS. 5A-5C disposed between the arms of a sternal retractor, in accordance with one embodiment of the present invention.
Figure 6B:
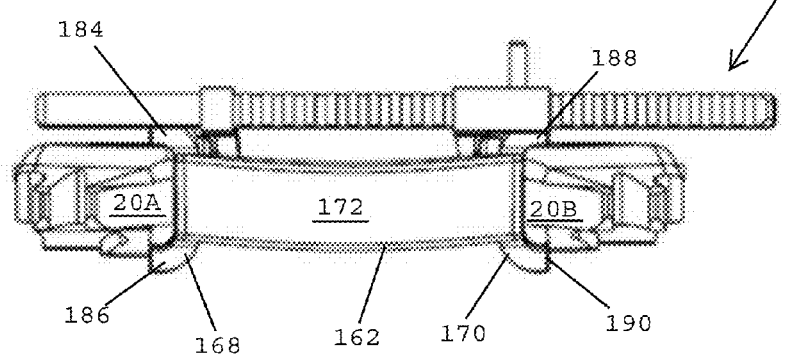

Referring to FIGS. 6A and 6B, in one embodiment, a sternum 20 (FIG. 1A) is split to provide a first half 20A and a second half 20B. The hemostatic insert 160 shown in FIGS. 5A-5C is inserted between the split sternum halves so that the first section 168 of the insert 160 engages the cut edge 24A of the first sternum half 20A and the second section 170 of the insert 160 engages the cut edge 24B of the second sternum half 20B. The connector section 172 is bent as the first and second sections 168, 170 of the hemostatic insert 160 are collapsed toward one another for insertion between the opposing cut edges 24A, 24B of the sternum 20. The C-shaped flanges 38A, 38B of the first retractor arm 32 (FIG. 2A) engage the rigid member 174 that backs the first section 168 of the insert and the C-shaped flanges 48A, 48B of the second retractor arm 42 (FIG. 2A) engage the rigid member 176 that backs the second section 170 of the insert 160. The pinion 56 of the retractor 30 may be engaged for moving the second arm 42 away from the first arm 32 for increasing the spacing between the opposed cut edges 24A, 24B of the respective sternum halves 20A, 20B.

Referring to FIG. 6B, the cut edge of the first sternum half 20A sits within the trough of the first section 168 so that it is bounded above and below by the upper flange 184 and the lower flange 186. The opposing cut edge of the second sternum half 20B sits within the trough of the second section 170 so that it is bounded by the upper flange 188 and the lower flange 190. The connector section 172 has resiliency and/or spring-like characteristics that normally urge the first section 168 away from the second section 170 as the flexible backing 162 of the flexible backing 162 seeks to return to a flat configuration. This resiliency holds the insert in place until the retractor arms are coupled with the first and second sections of the insert.

Figure 6C:
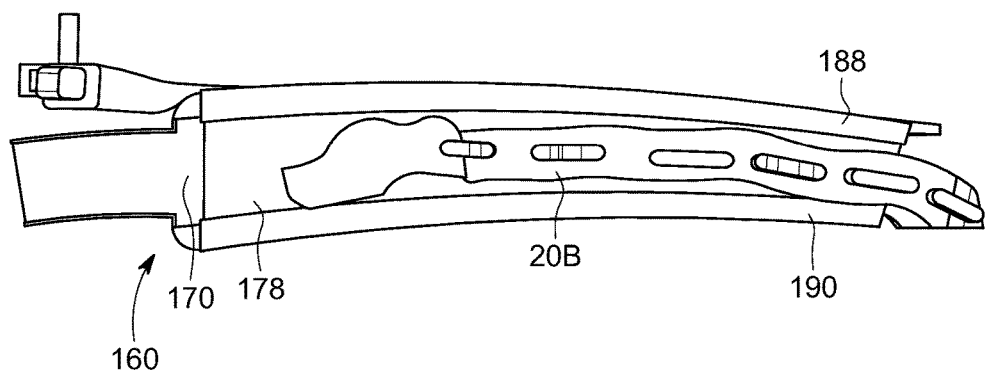

FIG. 6C shows the second split sternum half 20B disposed within the trough 178 of the second section 170 of the insert 160 with the cut edge of the second sternum half 20B disposed between the upper flange 188 and the lower flange 190 of the first section 170 of the insert 160.

Figure 7:
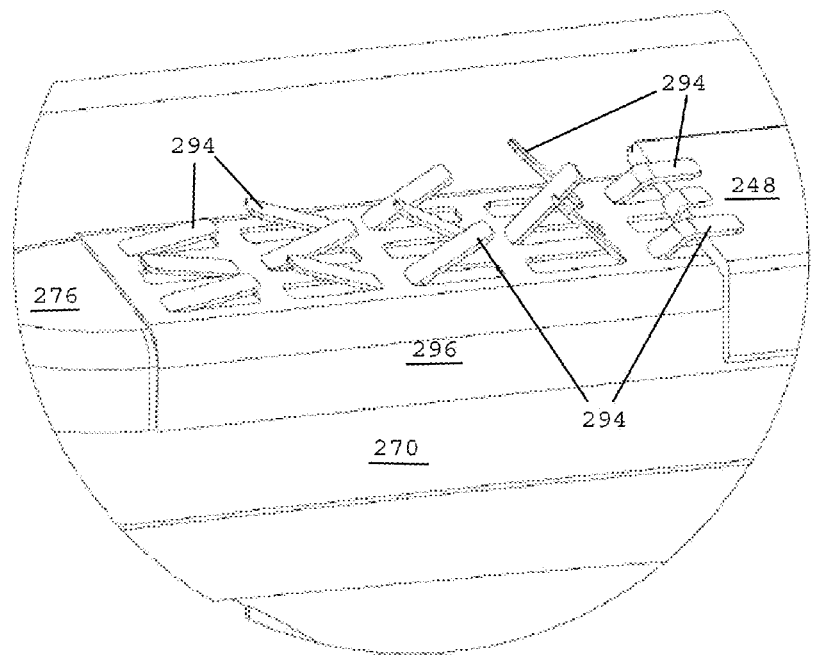
FIG. 7 shows an insert for a sternal retractor, the insert having malleable tabs, in accordance with one embodiment of the present invention.

Referring to FIG. 7, in one embodiment, an insert 260 for a sternal retractor desirably includes malleable tabs 294. In one embodiment, the malleable tabs are provided on a sleeve 296 that is attached with a rigid member 276. In one embodiment, after the rigid member 276 is received within the trough of a C-shaped flange 248 connected with a retractor arm, one or more of the malleable tabs 294 may be bent to wrap around the edge and/or back side surface of the C-shaped flange 248 to further secure the insert to the retractor arm and prevent shifting of the insert relative to the retractor arm.

Some surgical retractors on the market do not have adequately designed flanges that form a stable connection between the inserts and the retractor arms. Using malleable tabs enables surgical personnel to create a more reliable, stable connection between inserts and retractor arms, which prevents shifting or movement of the inserts relative to the retractor arms.

Figure 8A:
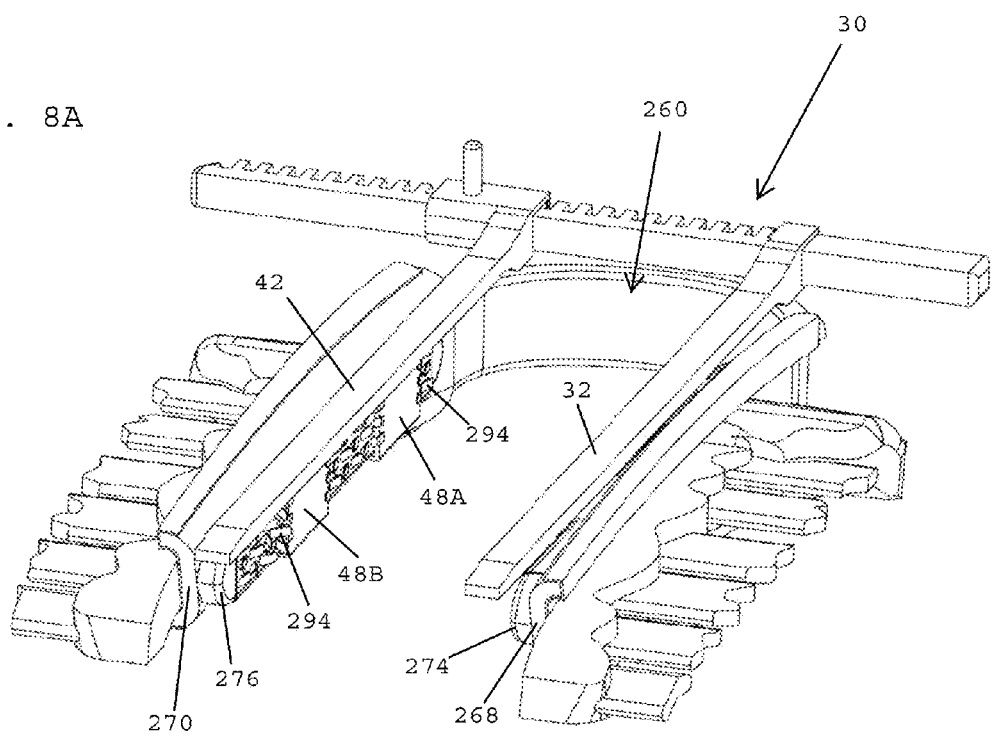
FIGS. 8A-8C show the insert of FIG. 7 secured to the arms of a sternal retractor using malleable tabs, in accordance with one embodiment of the present invention.
Figure 8B:
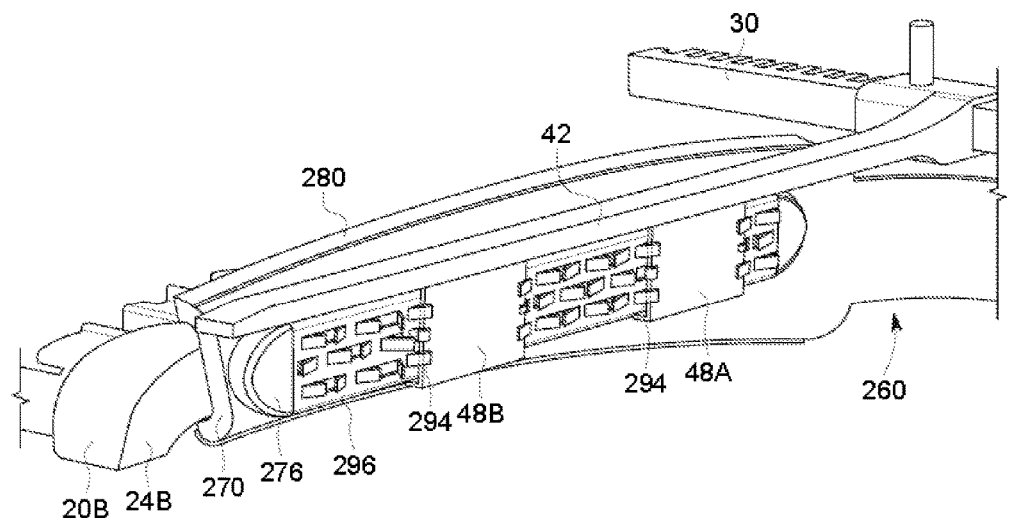
Figure 8C:
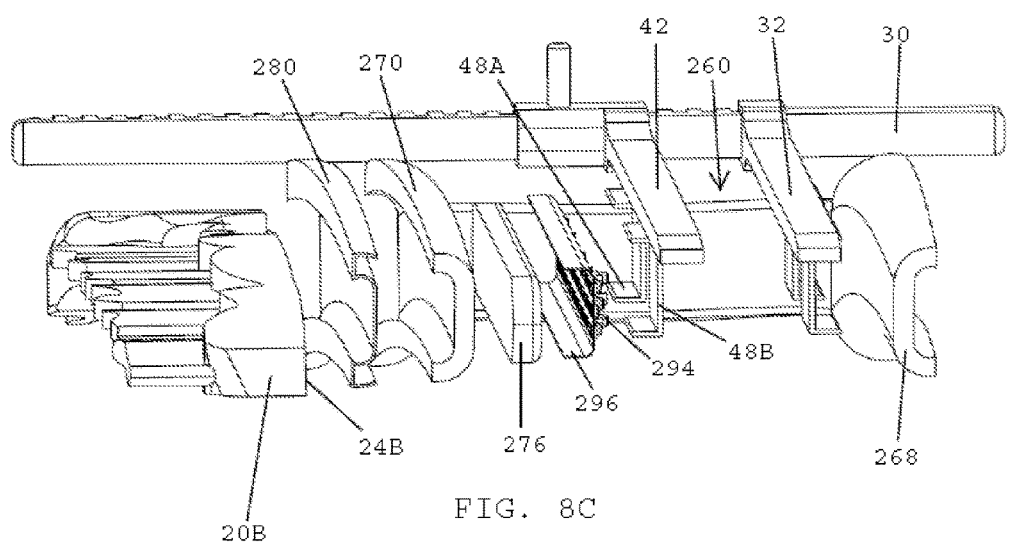

Referring to FIGS. 8A and 8B, in one embodiment, an insert 260 is disposed between first and second arms 32, 42 of a retractor 30. The second retractor arm 42 includes first and second C-shaped flanges 48A, 48B that are adapted to engage the rigid member 276 of the second section 270 of the insert 260. The first retractor arm 32 has a similar arrangement for engaging the rigid member 274 of the first section 268 of the insert 260.

In one embodiment, the malleable tabs 294 are bent so that they overlie edges of the first C-shaped flange 48A and/or the second C-shaped flange 48B. The direction that the malleable tabs 294 are bent depends upon the position of the respective C-shaped flanges 48A, 48B relative to the tabs. Thus, tabs may be bent proximally or distally. In one embodiment, the tabs 294 prevent the insert 260 from shifting or moving relative to the retractor arms.

Figure 9A:
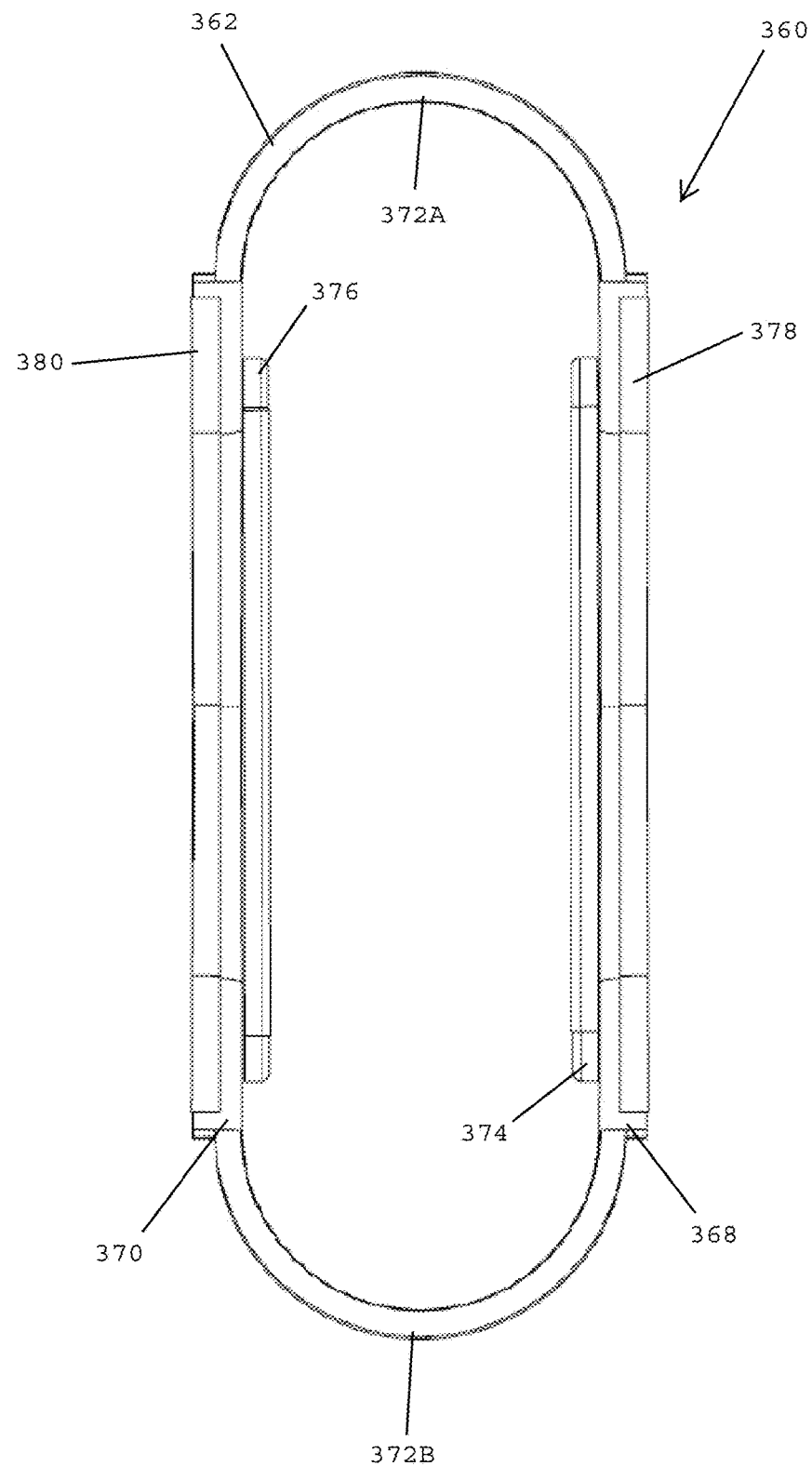
FIGS. 9A and 9B show an insert for a sternal retractor, in accordance with one embodiment of the present invention.
Figure 9B:
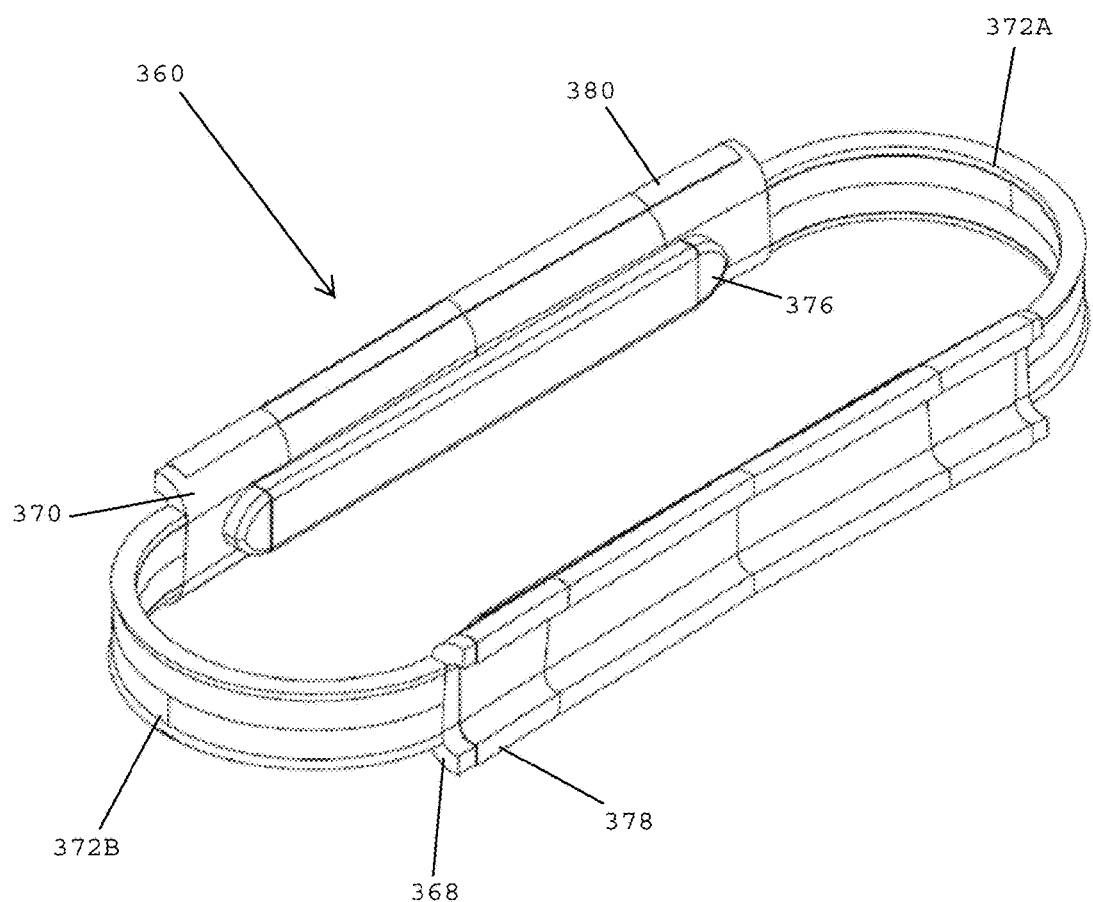

Referring to FIGS. 9A and 9B, a hemostatic insert 360 for use with a sternal retractor preferably includes a first section 368 adapted to engage a first arm of a sternal retractor and a second section 370 adapted to engage a second arm of a sternal retractor. The insert 360 includes a first connector section 372A that interconnects proximal ends of the first and second sections 368, 370 and a second connector section 372B that interconnects the distal ends of the first and second sections 368, 370 of the insert 360. The first section 368 of the insert includes similar structure as described above including a flexible backing, a rigid member 374 and a hemostatic layer 378 that overlies the outer surface of the flexible backing of the first section 368. The insert 360 also includes a second rigid member 376 attached to the inner side of the second section 370 of the flexible backing and a hemostatic layer 380 that overlies an outer surface of the flexible backing at the second section 370. The first and second sections may also have malleable tabs for forming an enhanced attachment between the insert and retractor arms of a surgical retractor.

In one embodiment, the rigid members 374, 376 are adapted to be engaged by C-shaped flanges on first and second arms of a retractor, as shown and described herein.

The first and second connector sections 372A, 372B have resiliency and/or spring-like characteristics that enable the first and second sections 368, 370 of the insert 360 to be collapsed inwardly toward one another so that the insert may be positioned between opposing, cut edges of a sternum. When the collapsing force is released, the resilient connector sections 372A, 372B normally urge the first and second sections 368, 370 of the insert to move away from one another for self-seating the insert between the opposing, cut edges of a sternum.

Figure 10:
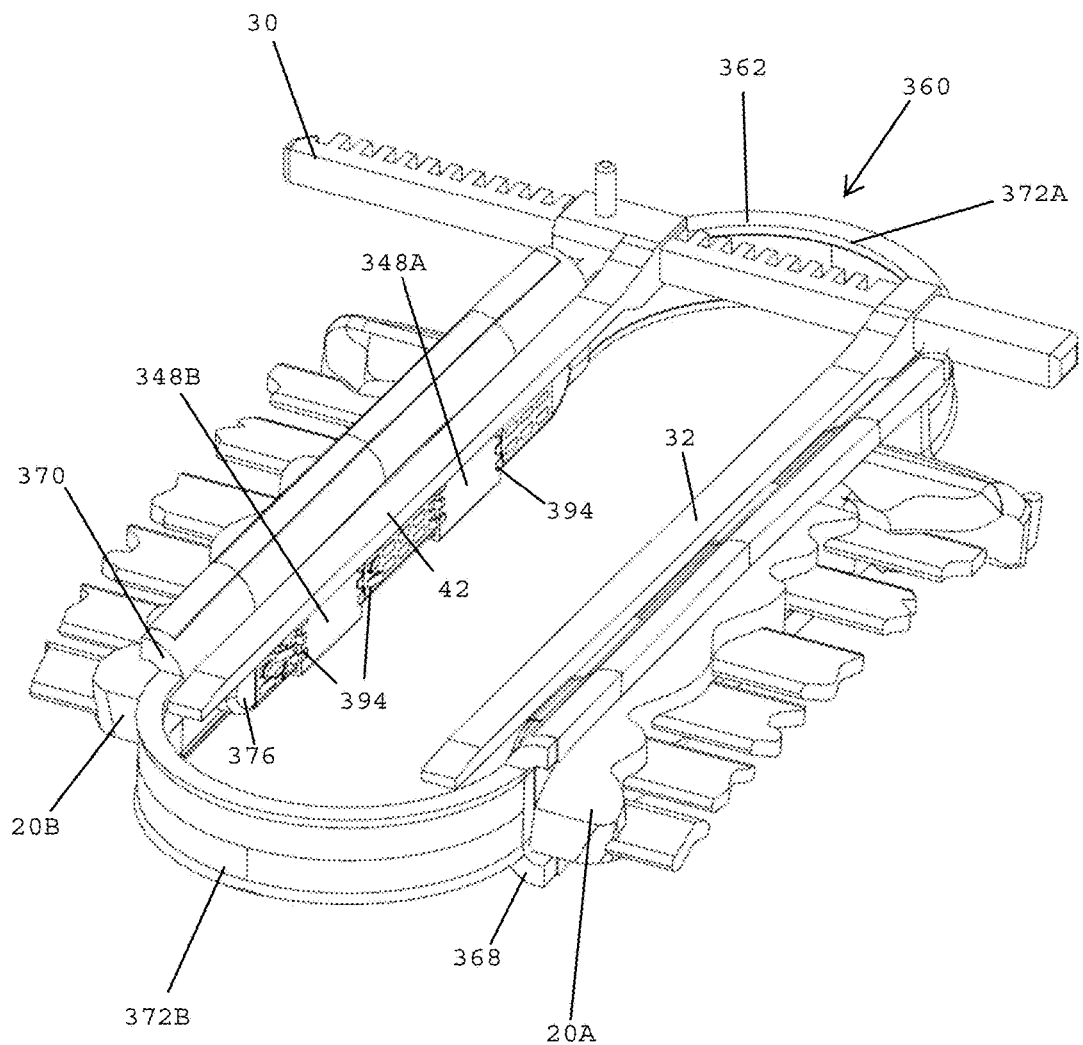
FIG. 10 shows the insert of FIGS. 9A and 9B disposed between the arms of a sternal retractor, in accordance with one embodiment of the present invention.

Referring to FIG. 10, in one embodiment, a sternum is split into a first half 20A and a second half 20B. The first section 368 of the insert 360 is positioned over the cut edge of the first half 20A of the sternum, and the second section 370 of the insert 360 is collapsed inwardly toward the first section 368 so that it may engage the cut edge of the second half 20B of the sternum. The first and second connector sections 372A, 372B may bend or fold as the first and second sections 368, 370 of the insert 360 are collapsed inwardly toward one another. Once the troughs of the respective first and second sections 368, 370 of the insert 360 are positioned against the opposing cut bone surfaces 22A, 22B, surgical personnel may release the insert 360 so that the resiliency of the connector sections 372A, 372B urge the first and second sections 368, 370 of the insert 360 away from one another and against the opposing cut edges of the split sternum. Thus, the hemostatic insert 360 disclosed herein has a self-seating capability, which holds the insert in place until the insert is attached to the arms 32, 42 of a retractor 30 (FIG. 2A).

In one embodiment, the rigid member 376 connected with the first section 370 of the insert 360 has malleable tabs 394 that may be bent or folded over the edges of the C-shaped flanges 348A, 348B of the second retractor arm 342. In one embodiment, the first arm 32 of the retractor 30 has similar features including the C-shaped flanges and the malleable tabs on a rigid member that backs the first section 368 of the insert 360. The malleable tabs preferably enhance the secure connection between the insert and the retractor arms.

In one embodiment, the flexible backing member 362 of the insert 360 may be treated with a chemical or solution that is activated immediately prior to insertion between a split sternum. The reactive chemical or solution may make one or more sections of the insert 360 more rigid after it is inserted into the surgical opening for holding the insert in place within the surgical opening. In one embodiment, only the first and second connector sections 372A, 372B of the flexible backing 362 are treated with a reactive chemical or solution for making those sections of the insert more rigid after insertion between the opposing edges of a split sternum.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A surgical retraction system comprising:
    a sternal retractor having a first retractor arm and a second retractor arm;
    an insert comprising
        a first section having a first rigid backing,
        a second section having a second rigid backing that is spaced from said first rigid backing, and
        a connector section comprising resilient material interconnecting proximal ends of said first and second sections, wherein said first section of said insert is coupled with said first retractor arm, said second section of said insert is coupled with said second retractor arm, and said connector section of said insert extends laterally between the proximal ends of said first and second sections of said insert.

2. The system as claimed in claim 1, wherein said resilient connector section of said insert enables said insert to flex between a flat configuration and a bent configuration, and wherein said resilient connector section urges said insert into the flat configuration when said first and second sections of said insert are unconstrained.

3. The system as claimed in claim 2, wherein said insert has a U-shape when in the bent configuration with said first section of said insert forming a first vertical leg of the U-shape, said second section of said insert forming a second vertical leg of the U-shape, and said connector section forming a curved base of the U-shape that extends laterally between the proximal ends of said first and second sections.

4. The system as claimed in claim 2, wherein when said insert is in the flat configuration said first section of said insert, said second section of said insert, and said connector section of said insert lie in a common plane.

5. The system as claimed in claim 1, wherein said insert comprises a hemostatic agent.

6. The system as claimed in claim 5, wherein said insert comprises:
    a flexible backing having a first major surface, a second major surface, a first end defining said first section of said insert, a second end defining said second section of said insert, and said connector section interconnecting said first and second ends of said flexible backing;
    a first rigid member aligned with the first end of said flexible backing and attached to the second major surface of said flexible backing to form said first rigid backing of said first section of said insert; and
    a second rigid member aligned with the second end of said flexible backing and attached to the second major surface of said flexible backing to form said second rigid backing of said second section of said insert.

7. The system as claimed in claim 6, further comprising:
    a first layer of material containing said hemostatic agent covering the first major surface of said flexible backing at the first end of said flexible backing; and
    a second layer of material containing said hemostatic agent covering the first major surface of said flexible backing at the second end of said flexible backing.

8. The system as claimed in claim 1, further comprising:
    said first retractor arm including at least one first arm flange, wherein said first section of said insert is coupled with said at least one first arm flange; and
    said second retractor arm including at least one second arm flange, wherein said second section of said insert is coupled with said at least one second arm flange.

9. The system as claimed in claim 8, wherein said first rigid backing comprises a plurality of first malleable tabs, and said second rigid backing comprises a plurality of second malleable tabs.

10. The system as claimed in claim 9, further comprising:
    a first metal sleeve connected with said first rigid backing, said first metal sleeve comprising said first malleable tabs; and a second metal sleeve connected with said second rigid backing, said second metal sleeve comprising said second malleable tabs.

11. The system as claimed in claim 9, wherein one or more of said first malleable tabs are in contact with said at least one first arm flange for securing said first section of said insert to said first retractor arm, and wherein one or more of said second malleable tabs are in contact with said at least one second arm flange for securing said second section of said insert to said second retractor arm.

12. The system as claimed in claim 1, further comprising a second connector section interconnecting distal ends of said first and second sections of said insert, wherein said second connector section comprises a resilient material.

13. The system as claimed in claim 12, wherein said insert has an oval shape and wherein said resilient first and second connector sections enable said first and second sections of said insert to be compressed toward one another.

14. A surgical retraction system comprising:
a sternal retractor having a first retractor arm and a second retractor arm;
an insert comprising
a flexible backing having a front surface, a back surface, a first end, a second end, and a connector section interconnecting said first and second ends of said flexible backing,
a first rigid member aligned with the first end of said flexible backing and attached to the back surface of said flexible backing to form a first rigid section of said insert, and
a second rigid member aligned with the second end of said flexible backing and attached to the back surface of said flexible backing to form a second rigid section of said insert;
wherein said first rigid section of said insert is coupled with said first retractor arm, said second rigid section of said insert is coupled with said second retractor arm, and said connector section extends laterally between proximal ends of said first and second rigid sections.

15. The system as claimed in claim 14, wherein said connector section comprises resilient material that urges said first and second rigid sections of said insert away from one another.

16. The system as claimed in claim 14, wherein said insert is bendable from a flat configuration to a bent configuration, and wherein said connector section comprises resilient material that urges said insert into the flat configuration when said first and second rigid sections of said insert are unconstrained.

17. The system as claimed in claim 16, wherein said insert has a U-shape when in the bent configuration with said first rigid section of said insert forming a first vertical leg of the U-shape, said second rigid section of said insert forming a second vertical leg of the U-shape, and said resilient connector section forming a curved base of the U-shape that extends laterally between the proximal ends of said first and second rigid sections.

18. The system as claimed in claim 14, further comprising:
a first layer of material comprising a hemostatic agent covering said first rigid section of said insert; and
a second layer of material comprising a hemostatic agent covering said second rigid section of said insert.

19. The system as claimed in claim 14, wherein said first rigid member comprises a plurality of first malleable tabs, and said second rigid member comprises a plurality of second malleable tabs, wherein one or more of said first malleable tabs are in contact with said first retractor arm for securing said first rigid member to said first retractor arm, and wherein one or more of said second malleable tabs are in contact with said second retractor arm for securing said second rigid member to said second retractor arm.

20. A surgical retraction system comprising:
a sternal retractor including a first retractor arm with at least one first arm flange and a second retractor arm with at least one second arm flange;
an insert assembled with said sternal retractor, said insert comprising
a first section having a first rigid backing, said first rigid backing comprising one or more first malleable tabs in contact with said at least one first arm flange for securing said first section of said insert to said first retractor arm,
a second section having a second rigid backing that is spaced from said first rigid backing, said second rigid backing comprising one or more second malleable tabs in contact with said at least one second arm flange for securing said second section of said insert to said second retractor arm, and
a flexible connector section interconnecting proximal ends of said first and second sections of said insert, wherein said connector section comprises a resilient material.

21. The system as claimed in claim 20, further comprising a second flexible connector section interconnecting distal ends of said first and second sections of said insert, wherein said second connector section comprises a resilient material, wherein said insert has an oval shape, and wherein said first and second resilient connector sections are flexible for allowing said first and second sections of said insert to be compressed toward one another.

\* \* \* \* \*